March 20, 1956 E. S. BOERNER Plant Pat. 1,461
CHRYSANTHEMUM PLANT
Filed March 31, 1955
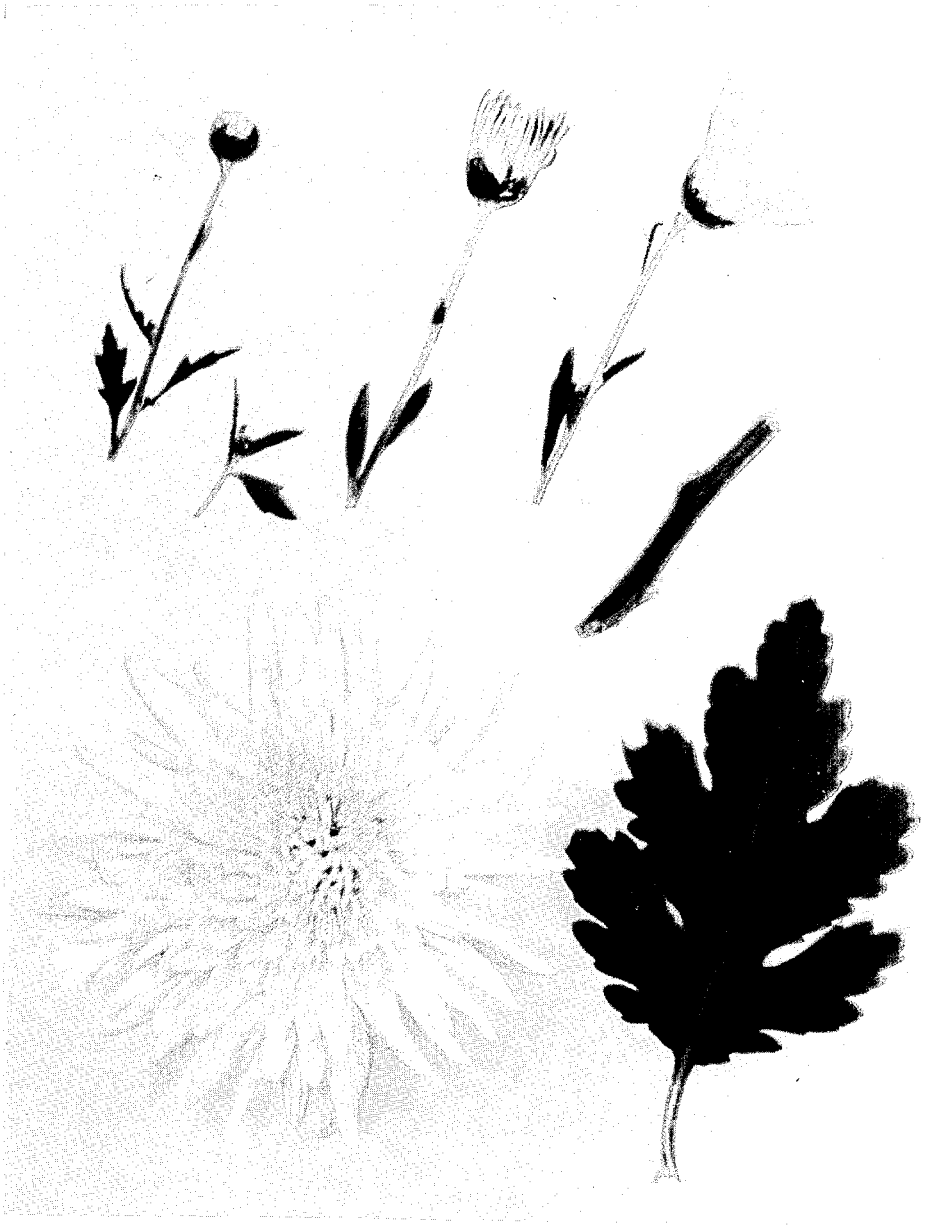
Inventor.
E. S. Boerner
By: Robb & Robb
Attorneys.

United States Patent Office

Plant Pat. 1,461
Patented Mar. 20, 1956

1,461

CHRYSANTHEMUM PLANT

Eugene S. Boerner, Newark, N. Y., assignor to Jackson & Perkins Company, Newark, N. Y., a corporation of New York Application March 31, 1955, Serial No. 498,465

1 Claim. (Cl. 47—60)

The present invention relates to a new and distinct variety of chrysanthemum plant of the decorative type which was originated by me by crossing the well-known variety "September Dawn" (unpatented) with an unnamed and unpatented large-flowered Hortorum seedling.

The primary objective in making this cross was to produce a new larger-flowered chrysanthemum variety having the floriferousness of the parent variety "September Dawn," but which bears flowers of a different and more distinctive color. This objective was fully achieved as evidenced by the following unique combination of outstanding characteristics with which my new variety is endowed:

(1) The relatively large size of the plant;

(2) The upright habit of growth of the plant, ranging in height from 30 to 36 inches;

(3) The relatively long flowering stems of the plant;

(4) The cluster habit and relatively large size of the flowers on each stem;

(5) The distinctive coloring of the flowers which, in the half-open bud stage are Apricot Yellow, lightly overcast with Apricot Orange in general color tonality, and in the open-flower stage are Grenadine Red, lightly overcast with Bittersweet Orange in general color tonality; and (6) The spicy fragrance of the flowers.

The foregoing characteristics definitely distinguish my new variety from its parents, as well as from all other varieties of which I am aware, and asexual reproduction of the new variety by top cuttings and also by underground runners, as performed by me at Newark, New York, shows that the foregoing characteristics and distinctions come true to form and are established and transmitted through succeeding propagations.

The accompanying drawing shows typical specimens of the vegetative growth and flowers of my new variety in different stages of development and as depicted in color as nearly true as it is reasonably possible to make the same in a color illustration of this character.

The following is a detailed description of my new variety, with color terminology in accordance with Ridgway's Color Standards and Nomenclature:

Parentage: "September Dawn" × an unnamed large-flowered Hortorum seedling.

Classification: Decorative type.

Growth: Upright; strong; ranging in height from 30 to 36 inches.

Cold resistance: Winter-hardy, with frost resistant flowers, as compared with other varieties grown under comparable cultural conditions at Newark, New York.

Blooming period: In the Newark, New York, climatic area, blooming starts about the end of September and the plant is very free-blooming until severe freezing temperatures in October or November of the average season.

FLOWER (Observations made from specimens grown in a field at Newark, New York.)

Bud:

*Color.*—When sepals first divide—Apricot Orange, Plate 14. When petals begin to unfurl—Nopal Red, Plate 1. When half-blown: Inside—Apricot Yellow, Plate 4, lightly overcast with Apricot Orange, Plate 14; Outside—Grenadine Red, Plate 2, lightly overcast with Capucine Orange, Plate 3.

*Peduncle.*—Stiff; erect. Color—Kildare Green, Plate 31.

Bloom:

*Size.*—From 4 to 4½ inches.

*Stem.*—Long; strong.

*Form.*—Decorative type.

*Petalage.*—Double.

*Color.*—Center of flower—Scarlet, Plate 3. Outer petals—Capucine Orange, Plate 3, lightly overcast with Orange Buff, Plate 3. Base of petals—Light Green Yellow, Plate 5. Outside of petals—Light Ochraceous Salmon, Plate 15, lightly overcast with Orange Buff, Plate 3. Inside of petals—Grenadine Red, Plate 2, lightly overcast with Bittersweet Orange, Plate 2.

*Petals.*—Texture—stiff. Form—Oval.

*Fragrance.*—Spicy.

PLANT

Form: Rounded; upright; large.

Growth: Vigorous; free.

Foliage:

*Size.*—Large.

*Quantity.*—Normal.

*Color.*—Upper side—Dark Cress Green, Plate 31. Reverse side—Light Hellebore Green, Plate 17.

*Texture.*—Leathery.

I claim:

A new and distinct variety of chrysanthemum plant of the decorative type, substantially as herein shown and described, characterized particularly as to novelty by the relatively large size of the plant, its vigorous and upright growth, its relatively long flowering stems, the cluster habit and the relatively large size of the flowers on each stem, the distinctive Apricot Yellow, lightly overcast with Apricot Red general color tonality of its half-open buds and the Grenadine Red, lightly overcast with Bittersweet Orange general color tonality of its open flowers, and the spicy fragrance of the flowers.

No references cited.